(12) United States Patent
Olsen et al.

(10) Patent No.: US 11,491,254 B2
(45) Date of Patent: Nov. 8, 2022

(54) ADHESIVE WAFER WITH A NEUTRALIZER MATRIX

(71) Applicant: Coloplast A/S, Humlebaek (DK)

(72) Inventors: Henrik Olsen, Copenhagen OE (DK); Kristoffer Hansen, Naerum (DK); Simon Ravnbak, Copehagen (DK)

(73) Assignee: Coloplast A/S, Humlebaek (DK)

(*) Notice: Subject to any disclaimer, the term of this patent is extended or adjusted under 35 U.S.C. 154(b) by 267 days.

(21) Appl. No.: 16/761,817

(22) PCT Filed: Nov. 2, 2018

(86) PCT No.: PCT/DK2018/050278
§ 371 (c)(1),
(2) Date: May 6, 2020

(87) PCT Pub. No.: WO2019/091526
PCT Pub. Date: May 16, 2019

(65) Prior Publication Data
US 2021/0187155 A1   Jun. 24, 2021

(30) Foreign Application Priority Data
Nov. 8, 2018   (DK) .......................... PA 2017 70835

(51) Int. Cl.
| | | |
|---|---|---|
| *A61L 24/00* | (2006.01) | |
| *A61F 5/443* | (2006.01) | |
| *A61L 24/02* | (2006.01) | |
| *A61L 24/08* | (2006.01) | |
| *A61L 24/04* | (2006.01) | |
| *A61F 5/449* | (2006.01) | |

(52) U.S. Cl.
CPC ............ *A61L 24/001* (2013.01); *A61F 5/443* (2013.01); *A61L 24/0036* (2013.01); *A61L 24/02* (2013.01); *A61L 24/043* (2013.01); *A61L 24/08* (2013.01); *A61F 5/449* (2013.01)

(58) Field of Classification Search
CPC .... A61L 24/001; A61L 24/0036; A61L 24/02; A61L 24/043; A61L 24/08; A61F 5/443; A61F 5/449
See application file for complete search history.

(56) References Cited

U.S. PATENT DOCUMENTS

| | | |
|---|---|---|
| 3,077,192 A | 2/1963 | Berger |
| 3,302,647 A | 2/1967 | Marsan |
| (Continued) | | |

FOREIGN PATENT DOCUMENTS

| | | |
|---|---|---|
| CN | 1226178 A | 8/1999 |
| CN | 101163585 A | 4/2008 |
| (Continued) | | |

*Primary Examiner* — Guy K Townsend
(74) *Attorney, Agent, or Firm* — Coloplast Corp., Coloplast A/S; Nick Baumann

(57) ABSTRACT

An adhesive wafer for an ostomy device, the wafer comprising a skin-facing adhesive layer, a backing layer on a part of the non-skin-facing side of the adhesive layer, and a hole for accommodating a stoma. On the central portion of the wafer is located a release layer being configured to release a neutralizer. The release layer is in direct contact with the adhesive layer. The neutralizer is capable of neutralizing or at least minimizing the level of skin or adhesive aggressiveness of the output.

16 Claims, 8 Drawing Sheets

(56) References Cited

U.S. PATENT DOCUMENTS

| | | | |
|---|---|---|---|
| 3,522,808 A * | 8/1970 | Worcester | A61F 13/64 604/350 |
| 4,121,589 A | 10/1978 | McDonnell | |
| 4,723,952 A | 2/1988 | Esposito | |
| 5,942,186 A | 8/1999 | Sanada et al. | |
| 6,740,067 B2 | 5/2004 | Leise, Jr. et al. | |
| 7,858,836 B2 | 12/2010 | Sambasivam | |
| 8,652,825 B2 | 2/2014 | Eiteman et al. | |
| 9,084,696 B2 | 7/2015 | Luce | |
| 11,278,640 B2 * | 3/2022 | Stroebech | A61L 24/0015 |
| 2003/0004477 A1 * | 1/2003 | Nielsen | A61F 5/448 604/336 |
| 2003/0206944 A1 | 11/2003 | Cohen et al. | |
| 2006/0036223 A1 | 2/2006 | Baldwin et al. | |
| 2008/0063695 A1 | 3/2008 | Vitaris | |
| 2008/0195016 A1 | 8/2008 | Bottini | |
| 2008/0294129 A1 | 11/2008 | Giori et al. | |
| 2008/0319368 A1 | 12/2008 | Lykke et al. | |
| 2009/0010998 A1 | 1/2009 | Marchitto et al. | |
| 2010/0114044 A1 * | 5/2010 | Cramer | A61F 5/448 604/332 |
| 2010/0114045 A1 | 5/2010 | Cramer et al. | |
| 2010/0204664 A1 * | 8/2010 | Bach | A61F 5/445 604/344 |
| 2012/0041404 A1 * | 2/2012 | Bach | A61F 5/443 604/344 |
| 2012/0282321 A1 | 11/2012 | Cohen et al. | |
| 2012/0323193 A1 | 12/2012 | Johannison et al. | |
| 2013/0226063 A1 | 8/2013 | Taylor et al. | |
| 2013/0304008 A1 | 11/2013 | Hanuka et al. | |
| 2014/0163495 A1 * | 6/2014 | Nassopoulos | A61F 5/443 604/338 |
| 2016/0136323 A1 | 5/2016 | Leise, III | |
| 2018/0008451 A1 | 1/2018 | Stroebech | |
| 2019/0134256 A1 * | 5/2019 | Stroebech | A61L 24/0015 |
| 2020/0046541 A1 * | 2/2020 | Sund | A61F 5/445 |
| 2020/0246177 A1 * | 8/2020 | Hansen | A61B 5/4851 |
| 2021/0059912 A1 * | 3/2021 | Gallego | A61K 8/25 |
| 2021/0085510 A1 * | 3/2021 | Langhorn | A61F 5/4404 |
| 2021/0113362 A1 * | 4/2021 | Windeballe | A61F 5/0043 |
| 2021/0177641 A1 * | 6/2021 | Nielsen | A61F 13/0259 |
| 2021/0187155 A1 * | 6/2021 | Olsen | A61F 5/448 |
| 2021/0275342 A1 * | 9/2021 | Sund | A61F 5/443 |

FOREIGN PATENT DOCUMENTS

| | | | |
|---|---|---|---|
| CN | 101279102 A | 10/2008 | |
| CN | 102413797 A | 4/2012 | |
| CN | 107249519 A1 | 10/2017 | |
| EP | 0686381 A1 | 12/1995 | |
| EP | 1666008 A2 | 7/2006 | |
| EP | 1736136 A1 | 12/2006 | |
| EP | 1140009 B2 | 8/2010 | |
| EP | 2527823 A1 | 11/2012 | |
| GB | 1256866 A * | 12/1971 | A61F 5/445 |
| GB | 1274374 A | 5/1972 | |
| GB | 2418861 A1 | 4/2006 | |
| GB | 2422112 A | 7/2006 | |
| GB | 2533399 A | 6/2016 | |
| JP | 7275282 A2 | 10/1995 | |
| JP | 9173369 A | 7/1997 | |
| JP | 2010523274 A | 7/2010 | |
| RU | 1522475 A1 | 7/1995 | |
| RU | 2220685 C1 | 1/2004 | |
| RU | 2332975 C2 | 9/2008 | |
| WO | 9746265 A1 | 12/1997 | |
| WO | 0038747 A2 | 7/2000 | |
| WO | 0205735 A1 | 1/2002 | |
| WO | WO-0205735 A1 * | 1/2002 | A61F 5/448 |
| WO | 03026541 A1 | 4/2003 | |
| WO | 04080358 A1 | 9/2004 | |
| WO | 2007067111 A1 | 6/2007 | |
| WO | 101001650 A1 | 7/2007 | |
| WO | 2008124715 A2 | 10/2008 | |
| WO | 2013030581 A1 | 3/2013 | |
| WO | 2013130564 A1 | 9/2013 | |
| WO | 2014181338 A2 | 11/2014 | |
| WO | 2014181339 A2 | 11/2014 | |
| WO | 17044896 A1 | 3/2017 | |
| WO | 2017067558 A1 | 4/2017 | |
| WO | 17158340 A1 | 9/2017 | |
| WO | 2017190752 A1 | 11/2017 | |
| WO | 2018188705 A1 | 10/2018 | |
| WO | 2018188706 A1 | 10/2018 | |
| WO | 2018188707 A1 | 10/2018 | |

* cited by examiner

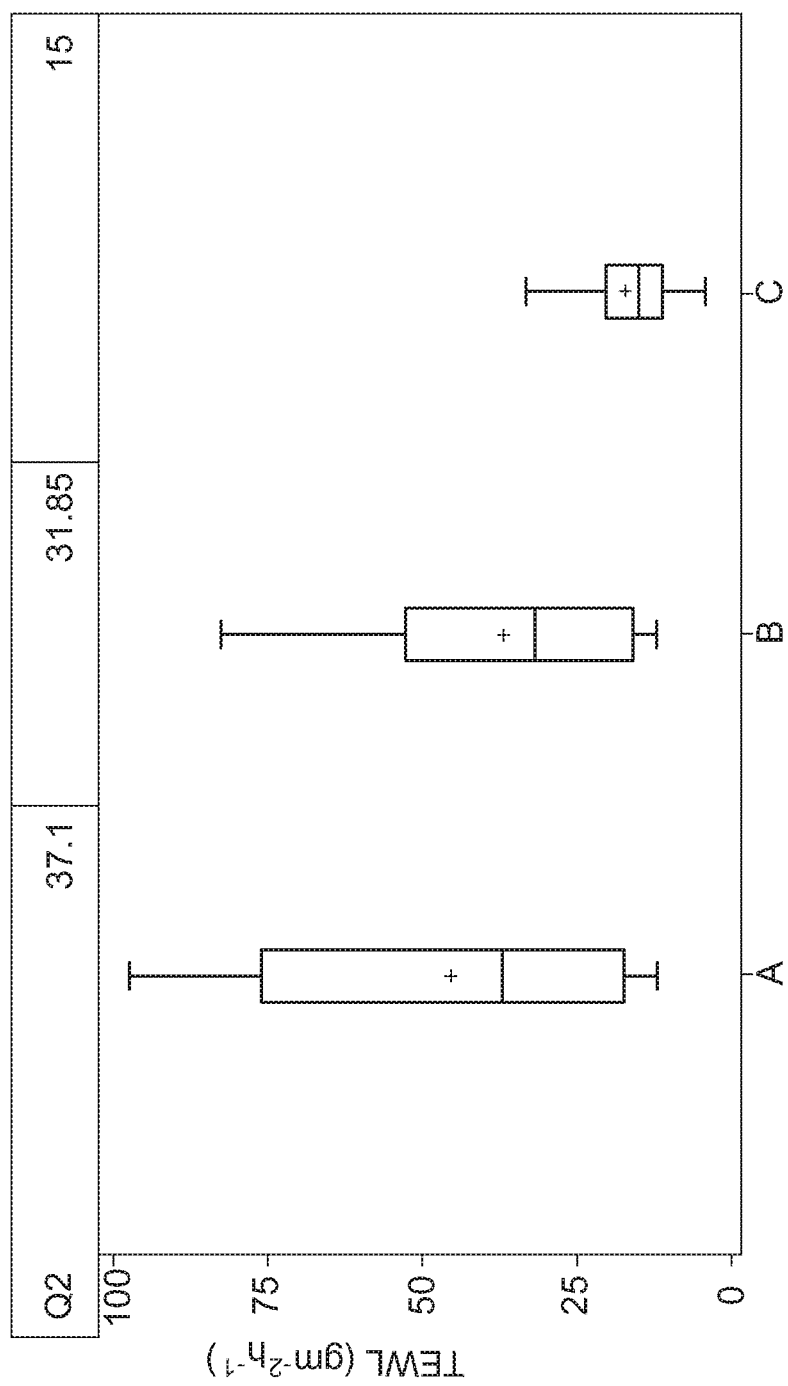

ADHESIVE WAFER WITH A NEUTRALIZER MATRIX

The invention relates to an adhesive wafer for an ostomy appliance and an ostomy appliance.

SUMMARY OF THE INVENTION

One aspect of the disclosure provides an adhesive wafer in accordance with the appended claim 1.

BRIEF DESCRIPTION OF THE DRAWING

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated, as they become better understood by reference to the following detailed description. The elements of the drawings are not necessarily to scale relative to each other. Like reference numerals designate corresponding similar parts.

FIGS. 4 and 5 show boxplots and statistical analysis of TEWL (transepidermal water loss).

DETAILED DESCRIPTION

Figure 1A:
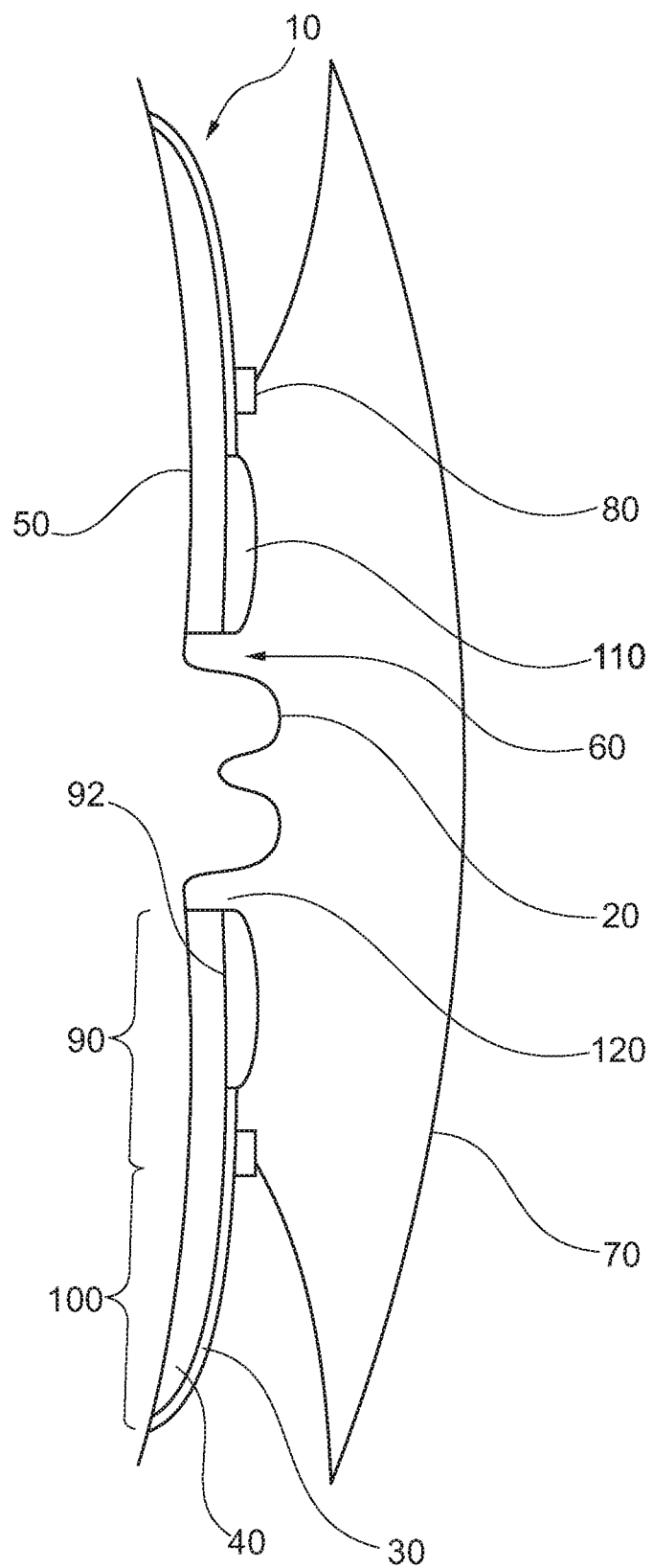
FIGS. 1a, 1b and 1c illustrate schematic cross-section views of different embodiments of a wafer.

In the following, whenever referring to the proximal side of a device or part of a device, the referral is to the skin-facing side, when the wafer or ostomy appliance is worn by a user. Likewise, whenever referring to the distal side of a device or part of a device, the referral is to the side facing away from the skin, when the wafer or ostomy appliance is worn by a user. In other words, the proximal side is the side closest to the user, when the wafer is fitted on a user and the distal side is the opposite side—the side furthest away from the user during use.

An axial direction is defined as the direction of the stoma, when the appliance is worn by a user. Thus, the axial direction is substantially perpendicular to a skin surface of a user, such as an abdominal skin surface. A radial direction is defined as transverse to the axial direction.

Prior to application to the skin a protective release liner may cover the skin contacting side of a pressure sensitive adhesive layer, to ensure that the properties of the adhesive are preserved and that the adhesive surface is not laid open until just before use. The release liner may suitably be a siliconised or fluorinated release liner, such as a siliconised or fluorinated craft paper, polyethylene, polypropylene or polyethylene terephthalate film. Suitably, the release liner is a siliconised polyethylene film, such as medium density polyethylene from the company Huhtamaki.

In the following, the words 'ostomy' and 'stoma' are used interchangeably without any intention to have different meanings.

By output is herein meant the effluent from a stoma, being faeces and/or urine in a more or less viscous form or mucins secreted from the epithelial layer of the alimentary canal. In the case of a colostomy, the output may be quite solid, whereas an ileostomy may produce more liquid output. The output may contain digestive fluids with enzymes and other components that may be aggressive to the skin and thus may cause maceration and contact dermatitis of the skin if brought into contact with it as well as the output may comprise components that may attack and degrade the adhesive.

Embodiments provide an adhesive wafer for an ostomy appliance, the wafer comprising a proximal adhesive layer, a backing layer on a portion of a distal side of the adhesive layer, and a through-going hole for accommodating a stoma, a connection zone, for attaching a collecting bag, circumferending the hole in a radial distance, and a release layer configured to releasing a neutralizer on the distal side of the adhesive layer, the release layer is located on at least a central portion of the backing layer, the central portion being defined as the area extending radially from the edge of the hole to a connection zone, wherein the release layer is in direct contact with the adhesive layer on the proximal surface.

In embodiments, the release layer is constituting a part of the distal surface of the wafer facing the interior of the collecting bag.

The adhesive layer being in direct contact with the release layer—without a backing layer in between, enables attachment of the release layer to the wafer. By having the release layer in direct contact with the adhesive layer, any material compatibility problems may be avoided.

In embodiments, a portion of the release layer is in direct contact with the distal surface of the adhesive layer and another part of proximal surface of the release layer is overlying a part of the distal surface of the backing layer. In embodiments, an entire proximal surface of the release layer is in direct contact with the distal surface of the adhesive layer.

The wafer may be a part of an ostomy appliance comprising an adhesive wafer and a collecting bag. The collecting bag may be detachably or permanently attached to the wafer along a connection zone surrounding the through-going hole in a radial distance and having an inlet corresponding with the hole in the wafer.

In some implementations, the wafer comprises a central portion, defined as the area extending radially from the edge of the through-going hole to the connection zone, and a peripheral portion, defined as an area of the wafer extending radially from the connection zone to an outer edge of the wafer.

When an ostomy wafer is applied to the skin surrounding a stoma, the proximal (skin-facing) adhesive layer provides a tight fit to the skin, in order to avoid the output from leaking under the wafer and damaging the skin and degrading the adhesive. Any output creeping under the wafer is to be avoided as much as possible as it may lead to maceration of the skin and degradation of the adhesive, resulting in leakage, unintended detachment of the wafer and discomfort to the user. Providing a release layer capable of releasing a neutralizer on the distal side of the wafer, the output will be neutralized before attacking the skin and/or the adhesive.

When fitting a through-going hole of an ostomy wafer to the area around a stoma, there will typically be a gap between an edge of the through-going hole in the wafer and the stoma. The stoma needs room to work due to inter alia peristaltic movements of the intestine; it enlarges when delivering output and shortens when not. In this gap, called the peristomal gap, output from the stoma can enter and over time degrade the adhesive layer as well as cause skin maceration. By providing a release layer configured to releasing a neutralizer at least at a central portion of the distal surface of the backing layer, the release layer is configured to get in contact with the output and release neutralizer to the peristomal gap, such that the skin and the adhesive of the wafer at the peristomal gap is protected against the damaging effects of the output. Some of the neutralizer can be flushed into the bag by the output, but most of the neutralizer flows into the peristomal gap and interacts with the output to neutralize its harmful components.

The output from the stoma may flow substantially continuously or it may enter the bag in bursts, e.g. depending on the type of stoma. If the user of the bag is in an upright position, continuous output may flow downwards due to gravity and primarily wet the part of the central portion of the wafer being below the stoma. However, the output may also creep upwards to wet the part of the central portion above the stoma. When coming in bursts, and inside a bag and with the distal wall of the bag close to the stoma, the output may spread all over the central portion of the backing layer, including also the area above the stoma. A user wearing a bag with clothing potentially pushing the bag wall towards the stoma, the output may for a period of time be trapped in and fill the volume defined by the wafer, the distal wall and the connection zone. Thus, the output may not immediately follow gravity but will also wet the area of the bag being above the stoma receiving hole and also the entire peristomal gap.

In embodiments, the release layer is at least located next to the hole, in the sense that the release layer is extending to the inner rim of the through-going hole. This enables the neutralizer to enter the peristomal gap when released from the release layer. By next to the hole is meant being extending radially inwards to define at least a part of the rim of the hole. In embodiments, the release layer is located on at least a part of the central portion of the distal portion of the adhesive layer. In embodiments, the portion of the distal surface of the adhesive layer not being provided with a release layer, is covered with a backing layer.

In embodiments, the release layer is contained in a recess in the adhesive layer. By providing the release layer in a recess, the release layer is controllable with regard to potential flowing because it is contained in the recess and the wafer can be stored and handled without the release layer unintentionally escaping. This is particularly advantageous if the material(s) of the release layer and/or the neutralizer contained in the release layer is of volatile character, or has a relatively low viscosity.

By recess is herein meant a depression in the adhesive layer, capable of containing at least a part of the release layer. In embodiments, the recess is a structure that is capable of containing a flowable substance, i.e. a cavity-like structure preventing the liquid substance from unintended flowing away from the recess.

In embodiments, the recess comprises a cavity embossed into the adhesive layer thereby providing a recess for containing the release layer. The distal surface of the backing layer and the release can be flush in the sense that the distal surface of the wafer is substantially planar.

In embodiments, the recess is form stable. The recess facilitates that the release layer stays in place during storage in case it tends to flow (is flowable) as well as it allows for the release layer to be thicker without compromising a total thickness of the wafer. In embodiments, the backing layer is flush with the release layer, providing a wafer with the same or uniform (equal) thickness over the central portion.

In embodiments, the backing layer is absent in the recess.

In embodiments, the distal surface of the wafer is substantially planar. In embodiments, the release layer protrudes from the distal surface of the wafer.

In embodiments, the release layer is located only in the central part of the adhesive wafer.

In embodiments, the release layer comprises a matrix with a neutralizer incorporated therein. The matrix serves as a carrier of the neutralizer and is capable of releasing the neutralizer.

By neutralizer is herein meant a neutralizing substance capable of neutralizing or at least minimizing the level of skin- or adhesive-aggressiveness of the output.

In embodiments, the neutralizer comprises a clay, such as organophilic clay, for example bentonite or synthetic clay such as laponite. Examples of such clays are disclosed in EP 1 140 009. In embodiments, the neutralizer may be potato-derived inhibitors or protease inhibitors. Examples of potato-derived inhibitors such as potato protein are disclosed in EP 1 736 136.

In embodiments, the matrix is a composition in which the neutralizer is incorporated. The neutralizer can be dissolved in the matrix or can be dispersed as particles in the matrix.

In embodiments, the release layer comprises coated neutralizer particles.

In embodiments, the matrix of the release layer is designed to release neutralizer when the release layer is exposed to certain conditions. Such conditions may for example be in the presence of output (being moist) from the stoma or in the presence of moisture.

Inside a collecting bag, the humidity will quickly reach about 100% humidity, so the presence of moisture is substantial. In embodiments where the release layer is sensitive to moisture, the release layer can be configured to initiate the release of neutralizer shortly after applying the wafer, due to the high humidity in the collecting bag.

In embodiments, the matrix is in the form of a gel, foam, film layer, paper or a coating. Such coating can for example be solid or a powder coating. In embodiments, the matrix and the neutralizer form a colloidal solution such as a sol.

In embodiments, the matrix comprises a water-soluble film such as a polyvinyl alcohol film, for example a Monosol 7031 film.

In embodiments, the matrix is soluble in water (moisture) or a component of the output. It can be slowly soluble, by slowly is herein meant that the matrix layer will not be washed away instantly, but slowly dissolves and provides a steady release of neutralizer over time, for example during wear time of the wafer. In embodiments, the matrix is configured to swell during absorption of moisture. In embodiments, the release layer is configured to be erodible when exposed to moisture. Hence, the release layer may decrease in thickness or even disappear over time when in use and exposed to moisture.

In embodiments, the matrix is configured to absorb moisture and turn into a gel like material when wetted. The matrix can be delivered in dry form and swell into a gel when brought into contact with moisture. In embodiments, the matrix is delivered as a gel. In embodiments, the gel is slowly soluble in water or in a component of the output or it can be insoluble, but able to release the neutralizer when exposed to stomal output or moisture. In embodiments, the matrix is a material capable of forming a gel when wetted or it may be in the form of a gel. Examples of suitable materials for the matrix composition may be polyethylene glycol (PEG), polyvinyl alcohol (PVA), polyvinyl pyrrolidone (PVP), ethylene vinyl acetate (EVA) based matrix and hydrocolloids such as CMC or gelatine.

In embodiments, the matrix comprises water-soluble or water-swellable polysaccharides and/or hydrocolloids. The polysaccharides or hydrocolloids may dissolve or hydrate when exposed to moisture from the output. When they are dissolved/hydrated, the neutralizer may be released.

In embodiments, the matrix comprises protein. In embodiments, the matrix comprises gelatine.

In embodiments, the matrix is substantially non-adhesive. By non-adhesive is meant that it is not adhesive, though it may, under certain conditions, become slightly sticky. A non-adhesive matrix is less prone to sticking to a distal wall of the collecting bag.

In embodiments, the release layer comprises a ring-shaped, oval, or roughly oval form. In embodiments, the adhesive element is asymmetric in shape.

In embodiments, the release layer comprises a cover layer or coating on the distal side. Such cover layer or coating can protect the release layer from sticking to a distal wall of the bag and/or control the speed (or rate) of the release of neutralizer from the release layer.

In embodiments, the adhesive layer of the central portion has a uniform thickness, i.e. the distance from the distal surface of the adhesive to the proximal surface of the adhesive layer measured in a straight line perpendicular to the surface of the adhesive layer. In embodiments, the uniform thickness of the adhesive layer is at least 50 micrometers, such as at least 100 micrometers, such as at least 200 micrometers, such as at least 300 micrometers, such as at least 400 micrometers, such as at least 500 micrometers, such as at least 750 micrometers.

In embodiments, the uniform thickness of the adhesive layer in the central portion is between 50 micrometers and 1,000 micrometers, such as 100-500 micrometers, such as 200-400 micrometers, such as 200-300 micrometers. In embodiments, the uniform thickness of the adhesive layer is 50-250 micrometers, 100-250 micrometers, 250-500 micrometers, 250-750 micrometers, 500-750 micrometers, 500-1,000 micrometers, 500-1,500 micrometers, 500-2,000 micrometers, 600-1,500 micrometers, 1,000-1,500 micrometers, 1,000-1,500 micrometers, 1,000-2,000 micrometers, or 1,500-2,000 micrometers.

In embodiments, the adhesive layer of the central portion has a varied thickness. In embodiments, the release layer has maximum thickness of at least 50 micrometers, such as at least 100 micrometers, such as at least 200 micrometers, such as at least 300 micrometers, such as at least 400 micrometers, such as at least 500 micrometers, such as at least 750 micrometers, such as at least 1,000 micrometers, such as at least 1,500 micrometers, such as at least 2,000 micrometers. The maximum thickness of the adhesive layer may be between 50 micrometers and 1,000 micrometers, such as 100-500 micrometers, such as 200-400 micrometers, such as 200-300 micrometers. In embodiments, the maximum thickness of the adhesive layer is 50-250 micrometers, 100-250 micrometers, 250-500 micrometers, 250-750 micrometers, 500-750 micrometers, 500-1,000 micrometers, 500-1,500 micrometers, 500-2,000 micrometers, 1,000-1,500 micrometers, 1,000-1,500 micrometers, 1,000-2,000 micrometers, or 1,500-2,000 micrometers, or 1,500-3000, or 1,500-4,000 micrometers.

In embodiments, the release layer is in the form of a ring-shaped element located at the central portion of the adhesive wafer. Such a ring-shaped release layer could have a diameter of 50-150 mm, such as 50-120 mm, such as 50-100 mm, such as 50-75 mm. The ring-shaped release layer could for instance have a diameter of 50 mm, 60 mm, 70 mm, 80 mm, 90 mm, 100 mm, 120 mm, or 150 mm. The ring-shaped element could have a width of at least 10 mm, at least 20 mm, at least 30 mm, at least 40 mm, at least 50 mm, at least 60 mm, at least 70 mm, at least 80 mm, at least 90 mm, at least 100 mm, 10-20 mm, 10-30 mm, 10-50 mm, 10-100 mm, 20-30 mm, 20-40 mm, 20-50 mm, 20-100 mm, 30-40 mm, 30-50 mm, 30-100 mm, 40-50 mm, 40-100 mm, or 50-100 mm. The width of the release layer can be constant over the entire layer or it may vary.

In embodiments, the adhesive layer is disposed on the backing layer and covers the entire backing layer. In embodiments, the release layer is in the form of a disc-shaped element at the central portion of the distal surface of the adhesive wafer, in the area around the through-going hole and attached directly to, being in direct contact with the distal surface of the adhesive layer.

In embodiments, the adhesive layer extends over the entire area of the adhesive wafer.

In embodiments, the release layer is in the form of a ring-shaped element located at the central portion of the adhesive wafer. Such a ring-shaped release layer could have a diameter of 50-150 mm, such as 50-120 mm, such as 50-100 mm, such as 50-75 mm. The ring-shaped release layer could for instance have a diameter of 50 mm, 60 mm, 70 mm, 80 mm, 90 mm, 100 mm, 120 mm, or 150 mm.

Embodiments provide an ostomy appliance, the wafer comprising a proximal adhesive layer, a backing layer on a portion of a distal side of the adhesive layer, and a through-going hole for accommodating a stoma, a connection zone, for attaching a collecting bag, circumferending the hole in a radial distance, and a release layer configured to releasing a neutralizer on the distal side of the adhesive layer, the release layer is located on at least a central portion of the backing layer, the central portion being defined as the area extending radially from the edge of the hole to a connection zone, wherein the release layer is in direct contact with the adhesive layer on the proximal surface.

In embodiments, the release layer is constituting a part of the distal surface of the wafer.

The collecting bag usually comprises a proximal wall on the distal side and a distal wall on the proximal side. The walls may be made of gas- and liquid impermeable foil-material (for example of polyethylene (PE), polyvinyl-chloride (PVC) or ethylene-vinyl-acetate (EVA)) that is welded around the edges or the rim, so as to form a pouch defining a waste collection chamber. The collecting bag may be welded only partly around the rim so that an opening for emptying the bag is provided at the bottom of the bag. In that case, the collecting bag may be provided with means for closing that opening. The waste inlet opening is provided in the rear wall and placed in the upper part of the collecting bag, so that when a user stands up, the waste inlet opening will be above the midline of the collecting bag. This leaves a larger collecting volume below the waste inlet opening. Thus, the top of the collecting bag is defined as the part closest to the waste inlet opening, and the bottom is defined as the opposite part.

In embodiments, the backing layer is gas and water impermeable. In embodiments, the wafer comprises an adhesive layer proximal to the skin, a backing layer on a part of the distal surface of the adhesive layer and a release layer on at least a part of the distal surface of the adhesive layer. Thus, in embodiments, the release layer is configured to be furthest away from the skin and is located on the central portion of the backing layer defining a part of an inside surface of the collecting bag.

In embodiments, an ostomy appliance is produced by providing an adhesive wafer, the wafer comprising a proximal adhesive layer, a backing layer on the distal side of the adhesive layer, and a through-going hole for accommodating a stoma, attaching the distal wall of a collecting bag along a connection zone on the backing layer, for example by welding, providing a release layer on the distal side of the central portion of the backing layer and optionally extending further radially to cover at least a part of the distal wall, and then superimposing the distal wall over the distal wall and welding the distal wall and the distal wall together along the rim to provide a closed collecting bag.

Disclosed is a method of protecting the peristomal skin of a user, the method comprising the following steps: providing an ostomy appliance comprising a collecting bag and an adhesive wafer, the wafer comprising a proximal adhesive layer, a backing layer on a part of the distal side of the adhesive layer, and a through-going hole for accommodating a stoma, and a release layer configured to releasing a neutralizer on the distal side of the adhesive layer, the release layer being in direct contact with the adhesive layer on the proximal surface; optionally adapting the size of the through-going hole to fit a stoma; and attaching the wafer to the skin around a stoma. When output from the stoma seeps into the peristomal gap between the through-going hole and the stoma, it flushes over the release layer and acts to release the neutralizer into the peristomal gap. The aggressive output from the stoma is neutralized before or shortly after reaching direct skin contact at the peristomal gap and the skin is free from or less prone to irritation due to the contact with the output.

Embodiments, and features of the various exemplary embodiments described in this application, may be combined with each other ("mixed and matched"), unless specifically noted otherwise.

DETAILED DESCRIPTION OF THE DRAWING

In the following detailed description, reference is made to the accompanying drawings. The drawings form a part of this specification and illustrate exemplary embodiments for practicing the invention. Directional terminology, such as "top," "bottom," "front," "back," etc., is used with reference to the orientation of the figures being described. Because components of embodiments can be positioned in a number of orientations, the directional terminology is used for purposes of illustration and is in no way limiting. It is to be understood that other embodiments may be utilized and structural or logical changes may be made without departing from the scope of the invention. The detailed description describes examples for practicing the invention and is not to be read to limit the scope of the invention. The scope of the invention is defined by the attached claims.

Initially, it shall be noted that the figures are schematic illustrations intended only to address the principles and functions of the wafer according to the invention and are not to be considered limiting to the scope of the attached claims. Furthermore, the figures and particularly the individually illustrated elements are not necessarily to scale, neither individually nor in relation to each other.

In FIG. 1a is shown a cross-sectional view of an ostomy appliance. The appliance comprises an adhesive wafer 10 having a proximal layer of adhesive 40 facing the skin for attaching the wafer to the skin 50 surrounding a stoma 20. A backing layer 30 is covering a part of the distal surface of the adhesive layer 40. A central trough-going hole 60 is provided in the wafer 10 for accommodating a stoma 20. The size of the trough-going hole 60 may be adapted by cutting to tailor fit the hole 60 to the stoma 20. The appliance includes a collecting bag 70, the bag 70 connected to the wafer 10 along a connection zone 80 circumferencing the hole 60 in a radial distance. The bag 70 may be detachably connected to the wafer 10 such that the bag 70 can be detached from the wafer 10 and exchanged, or the bag 70 may be inseparably connected to the wafer 10, for example by welding. The wafer 10 comprises a central portion 90, defined as the area extending radially from the hole 60 to the connection zone 80 and a peripheral portion 100, defined as the area extending radially from the connection zone 80 to the outer edge of the wafer 10. The backing layer 30 is absent at a portion 92 of the distal surface of the adhesive layer 40 surrounding the through-going hole. The portion 92 of the distal surface of the adhesive layer being without backing layer is provided with a release layer 110. The release layer 110 is in the form of a disc essentially covering the entire central portion 90 of the distal surface or primarily in the area of the distal surface being next to the trough-going hole 60. When cutting the trough-going hole 60, the release layer 110 is cut too. When output from the stoma 20 flows from the stoma and over the release layer 110, the release layer 110 releases the neutralizer which enters the peristomal gap 120 between the edge of the hole 60 and the stoma 20.

Figure 1B:
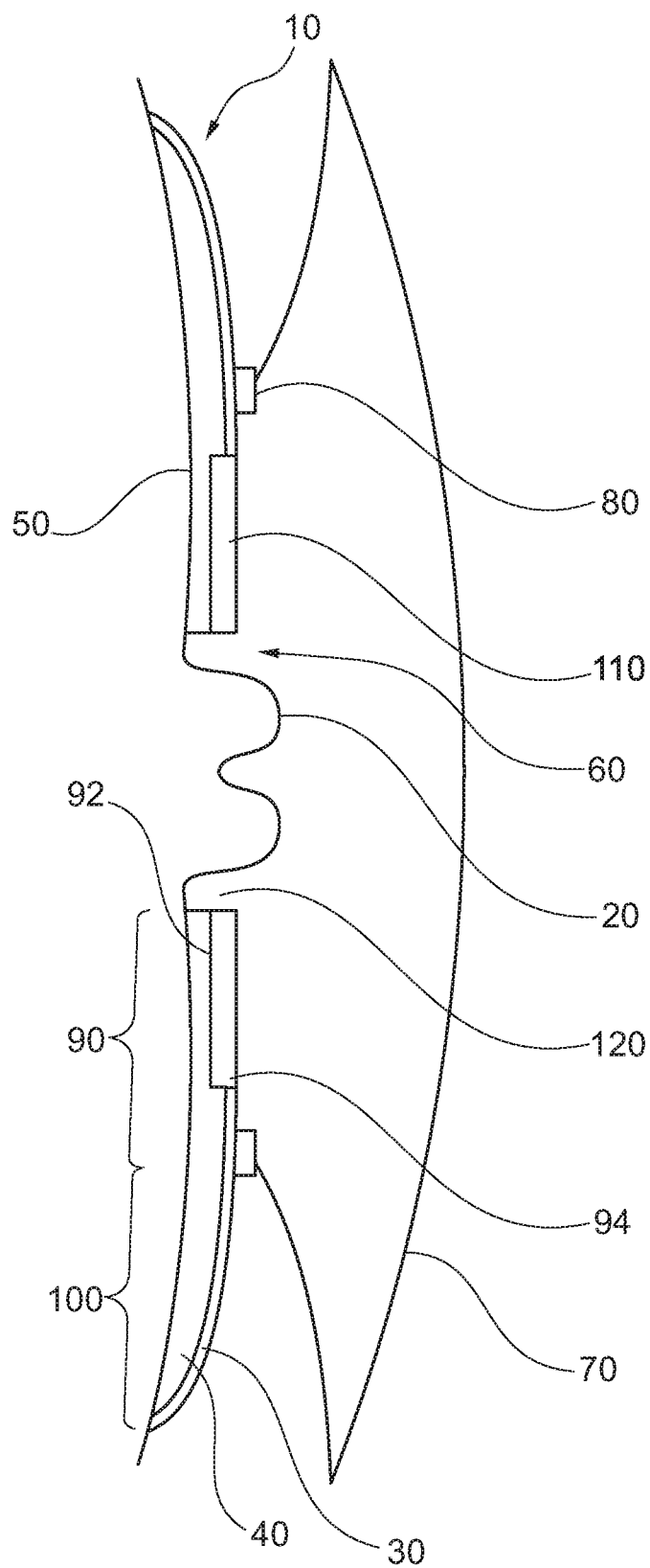

In FIG. 1b is shown another embodiment of an adhesive wafer where the release layer 110 is accommodated in a recess 94 in the adhesive layer 40. The recess 94 is in the form of a cavity in the adhesive layer 40. The release layer 110 is in direct contact with the adhesive layer 40, the backing layer 30 is absent in the cavity. In the shown embodiment, the distal surface of the wafer 10 is of uniform (equal) thickness over the entire central portion 90, providing for the distal surface of the wafer 10 to be substantially planar.

Figure 1C:
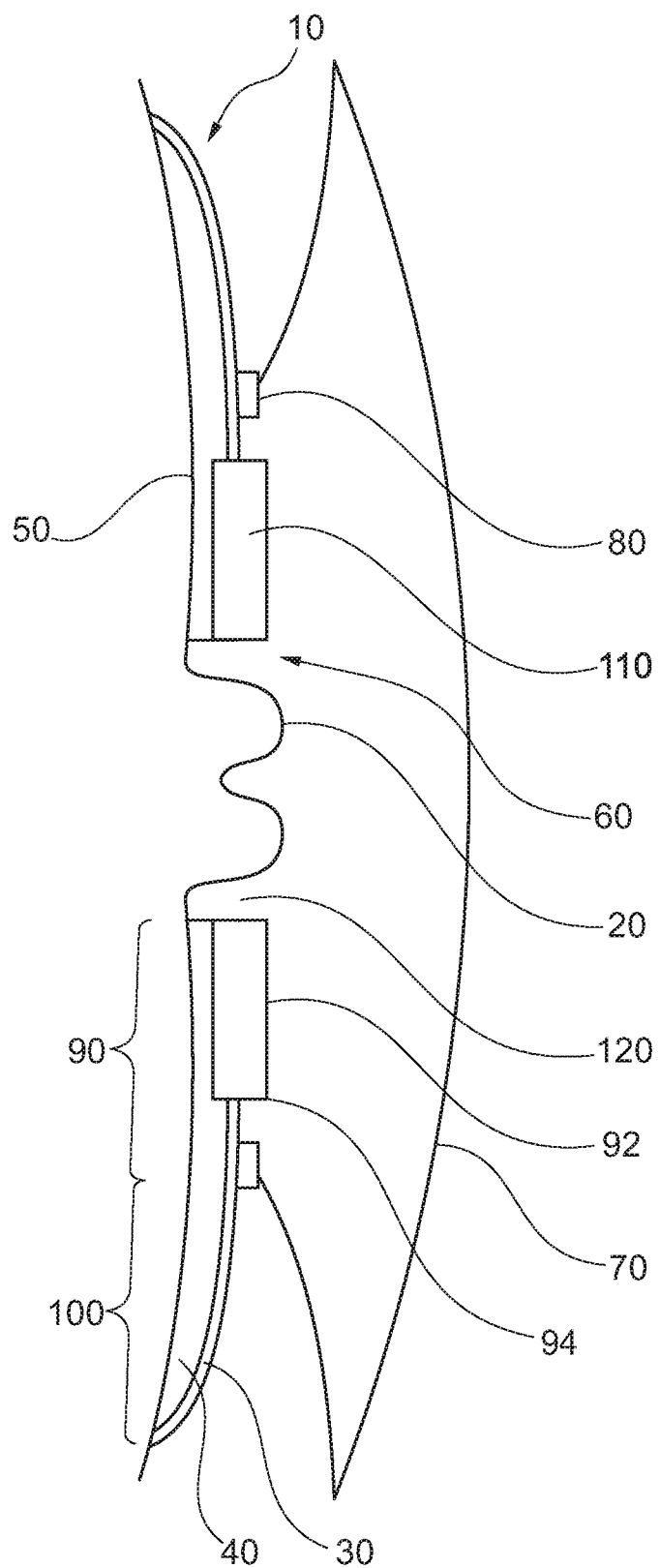

In FIG. 1c is shown yet another embodiment of an adhesive wafer where the release layer 110 is partly accommodated in a recess 94 in the adhesive layer 40. The recess 94 is in the form of a cavity in the adhesive layer 40. The release layer 110 is in direct contact with the adhesive layer 40, the backing layer 30 is absent in the recess 94. In the shown embodiment, the combined thickness of the release layer 110 and the adhesive layer in the recess 94 is higher than the thickness of the combined adhesive and the backing layer 30 outside the recess, thus the release layer extends into the adhesive layer (via the recess) and protrudes from the surface of the wafer 10.

Figure 2:
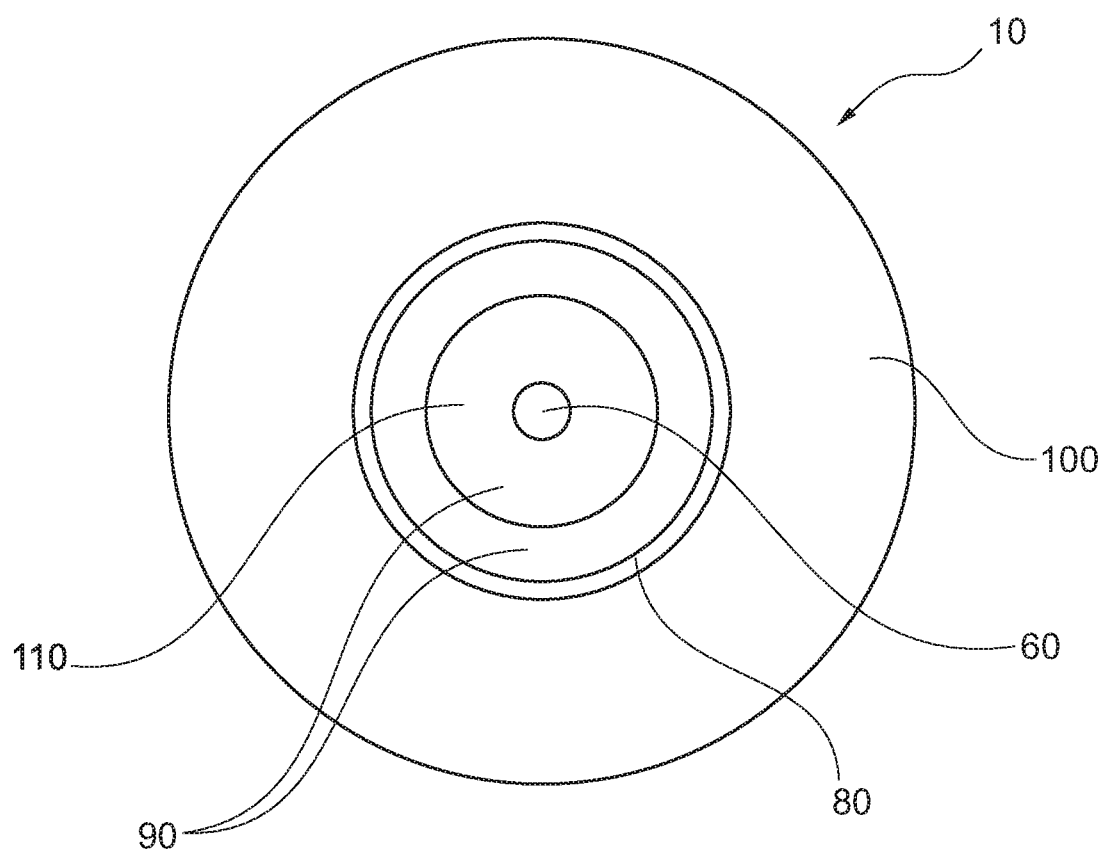
FIG. 2 illustrates a plan view of an embodiment of a wafer.

FIG. 2 shows an embodiment of an adhesive wafer 10 seen from the distal side, with a central portion 90 surrounding a hole 60 for accommodating a stoma 20, and a peripheral portion 100 surrounding the central portion. Along the transition between the central portion 90 and the peripheral portion 100 is the connection zone 80. The connection zone 80 may be in the form of a coupling for attaching a collecting bag (not shown). On a part of the distal surface of the central portion 90, closest to the hole 60, is provided a release layer 110.

EXAMPLE

An ostomy wafer (Sensura from Coloplast A/S) is provided. In a solution of PEG is suspended 1% particles of Protagold potato protein. The dispersion is placed onto the distal side of the central portion of the adhesive wafer and dried to form a 0.5 mm thick film layer.

Experimental

Distribution of Neutralizer (Flow Model)

A silicone cast of a stoma was made, and a hole was cut through it. One end of the stoma was attached to a syringe, which was used in order to control the flow through the stoma and creating an illusion of a flow of output from an intestine through the stoma.

The other end of the stoma was placed in a hole in a vertical plastic plate to simulate the stoma protruding through stomach wall.

Once the stoma model was set up, a Sensura wafer from Coloplast A/S, provided with a release layer on the distal surface of the central portion of the wafer was placed on the peristomal skin, with the release layer of the wafer being located on the surface facing away from the skin. The release layer comprised a matrix composition in the form of PEG (polyethylene glycol) and the neutralizer was represented by particles of amaranth (red colour dye) distributed homogenously in the matrix composition in a concentration of approximately 1%. The release layer was disposed on the central portion of the wafer in a thickness of approximately 0.5-1 mm.

Stomal output was represented by a viscous aqueous solution of carboxy methyl cellulose (CMC). When the output was pushed through the syringe, it flowed through the stoma, and down over the adhesive wafer and the release layer. When the flow was slowed down, it was possible to visually verify that the red colour also moved against the flow direction and towards the centre of the stoma, even despite of gravity. This indicates that at least a part of the neutralizer will flow from the release layer on the adhesive wafer to enter into the peristomal gap between the wafer and the stoma and will thereby be able to protect the skin in the peristomal area by neutralizing the output.

Figure 3A:
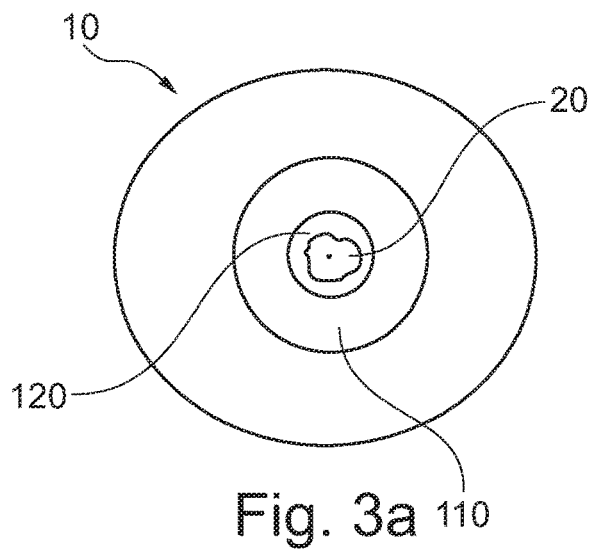
FIG. 3a-3c illustrate the flow of red dye in an embodiment of a wafer.
Figure 3B:
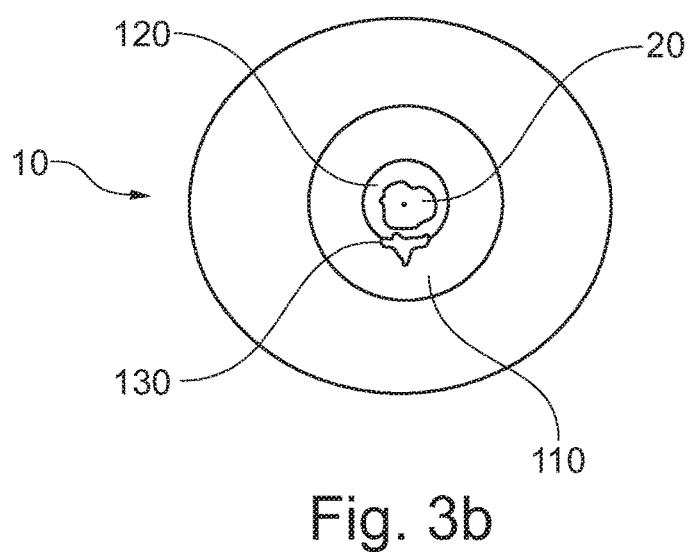
Figure 3C:
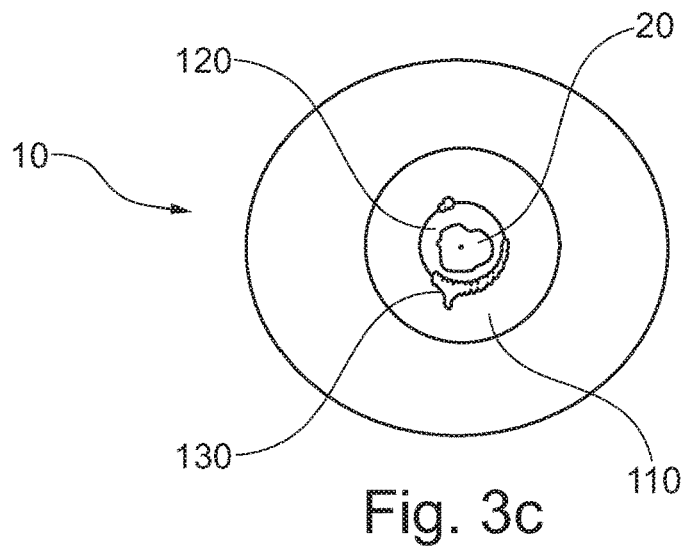
Figure 3D:
FIG. 3d is a photo of a stomal output flow model.

The phenomenon is illustrated in FIG. 3a-3c showing how the red dye distributes when the output is passed through the stoma. The wafer 10 was provided with a release layer 110 in which the content of neutralizer had been substituted with red dye as described above. FIG. 3a shows the wafer before output is introduced. In FIG. 3b, the output flows from the stoma 20 to wet the release layer 110, thereby releasing the red dye 130. As can be seen from the Figure, some of the dye passed downwards, due to gravity, whereas some of it flowed in the opposite direction, towards the stoma 20 and into the peristomal gap 120 between the stoma 20 and the wafer 10. Output may often come in bursts rather than a constant flow. Between the bursts, the neutralizer (red dye) flows into the peristomal gap 120. However, during a continuous flow of output from the stoma, retrograde flow is also seen. In FIG. 3c is shown how the neutralizer (red dye) 130 was released after a burst of output; the release was all the way round the stoma 20 and not only below the stoma 20. In FIG. 3d is shown a photo of the stoma model, with output flowing from the stoma and over the release layer.

Release of Neutralizer from the Release Layer

A composition was prepared as shown in Table 1:

TABLE 1

|  | Sample w/w |
| --- | --- |
| PEG | 41.7 |
| Laponite | 20.8 |
| Starch | 37.5 |

For testing the release of Laponite from the sample, 2 g of sample was placed in basket, 60 ml of PBS buffer (phosphate buffered saline) placed in cup and the basket was placed in the cup. The buffer was stirred by magnetic stirrer at 100 rpm and temperature was kept at 37° C. Measurements were in triplicates. The measuring method was yielding a 20% uncertainty. The buffer samples were analyzed for their content of Laponite using Atomic Absorption Spectroscopy AAS. After 2 hours, 79% of the Laponite was released to the buffer. Hence, the composition is capable of releasing the neutralizer into the buffer.

An Explorative Study Investigating Human Skin Reaction to Output

In a clinical setting the effect of feces on human skin was investigated using 22 subjects (users) having an ileostomy. At the beginning of the study all subjects had their ostomy product removed from the skin leaving the skin to acclimatize for 30 min. This was followed by measuring the transepidermal water loss (TEWL) at the beginning of the study to obtain the start value. The TEWL measurement describes the status of the skin barrier function and can be used to evaluate a damage to the skin.

All subjects had an ostomy product applied where part of the product was removed to make space for three collecting bags. These bags were in 12 of the subjects filled with respectively a buffer solution, the subject's own feces and a simulated feces solution containing trypsin and chymotrypsin. The bags were in the remaining 10 subjects filled with the same solutions but mixed with 5% of Laponite RD.

All bags were incubated on the peristomal skin for 6 hours before the bags were removed. The skin areas were cleaned and left to acclimatize for 30 min before the TEWL was measured again in the respective skin areas.

In FIG. 4 is shown a boxplot and a statistical analysis of TEWL on the peristomal area of the samples without Laponite RD (neutralizer).

The median TEWL results showed, as seen in FIG. 4, a significant higher value for skin incubated with real feces (A in the Figure) (P<0.001) as well as the simulated feces (B in the Figure) (P=0.001) compared to the buffer incubated skin (C in the Figure). This means that both real feces and simulated feces results in damage to the barrier of the skin. There was no difference between the damage seen with real feces or simulated feces (P=0.415).

Figure 5:
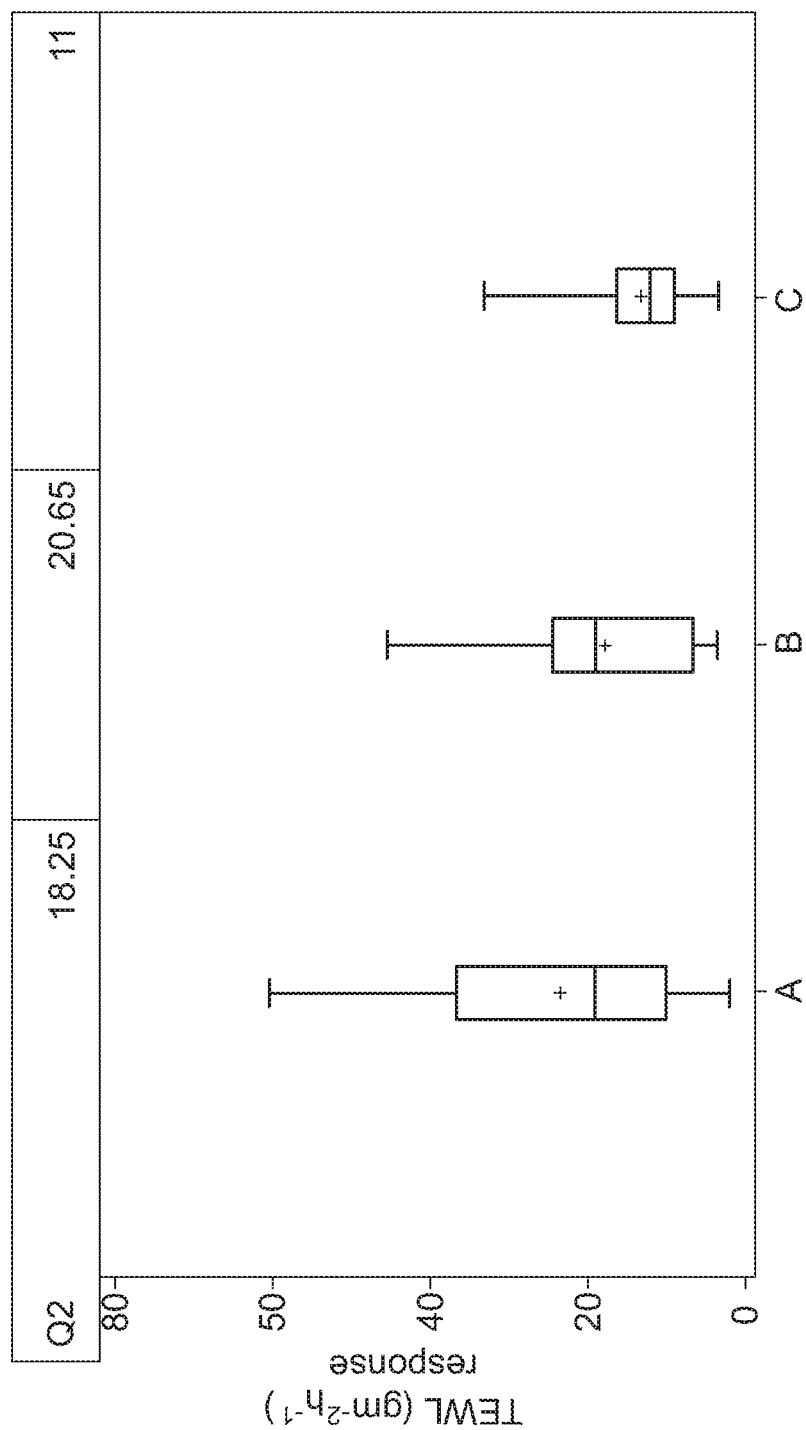

In FIG. 5 is shown a boxplot and statistical analysis of TEWL on the peristomal area of the samples containing Laponite RD (A', B' and C' in the Figure).

When the subject's own feces, simulated feces with enzymes or buffer were mixed with Laponite RD there were no significant difference between own feces (P=0.112) or simulated feces (P=0.175) compared to buffer with the Laponite RD. There was no significant difference between own feces or simulated output when Laponite RD were mixed into the solutions.

In conclusion, we saw a significant increase, compared to incubating with buffer, in the trans epidermal water loss (TEWL) from skin when the subject's own feces or simulated feces were incubated on the peristomal skin for 6 hours meaning a damage to the barrier of the skin.

Mixing the Laponite RD into the same solutions/suspensions did not influence the TEWL and thereby did not affect the barrier of the skin. Laponite RD mixed into feces or simulated feces neutralizes the damaging effect of these suspensions protected the skin from being damaged.

The invention claimed is:

1. An adhesive wafer for an ostomy appliance, the adhesive wafer comprising:
 a backing layer;
 an adhesive layer deposited on a proximal side of the backing layer;
 a hole formed through the adhesive wafer, with the hole sized to accommodate a stoma;
 a connection zone coupled to a distal side of the backing layer, where the connection zone is adapted to secure a waste collecting bag to the adhesive wafer; and
 a release layer deposited on a distal side of the adhesive layer, with the release layer in direct contact with the adhesive layer and located between the hole and the connection zone;
 wherein the release layer comprises a neutralizer that is adapted to neutralize output from the stoma.

2. The adhesive wafer of claim 1, further comprising:
 an ostomy bag attached to the connection zone;
 wherein the release layer is contained inside of the ostomy bag.

3. The adhesive wafer of claim 1, further comprising:
 a recess formed in the distal side of the adhesive layer, with the release layer deposited into the recess of the adhesive layer.

4. The adhesive wafer of claim 1, further comprising:
 a recess formed in the distal side of the adhesive layer between the hole and the connection zone, with the release layer deposited into the recess of the adhesive layer and the backing layer located to extend from the recess to an outer periphery of the adhesive wafer.

5. The adhesive wafer of claim 1, wherein a distal surface of the adhesive wafer is substantially planar.

6. The adhesive wafer of claim 1, wherein the release layer is located to extend from an edge of the hole to the connection zone.

7. The adhesive wafer of claim 1, wherein the neutralizer is incorporated in a matrix.

8. The adhesive wafer of claim 7, wherein the matrix is soluble in water.

9. The adhesive wafer of claim 7, wherein the matrix is a gel.

10. The adhesive wafer of claim 7, wherein the matrix is a foam.

11. The adhesive wafer of claim 7, wherein the matrix comprises a polysaccharide.

12. The adhesive wafer of claim 1, wherein the neutralizer is released in presence of moisture.

13. The adhesive wafer of claim 1, wherein the neutralizer comprises a clay.

14. The adhesive wafer of claim 1, wherein the neutralizer comprises potato derived inhibitors.

15. The adhesive wafer of claim 1, wherein the release layer is substantially non-adhesive.

16. The adhesive wafer of claim 1, wherein the release layer is deposited on the distal side of the adhesive layer and the distal side of the backing layer.

* * * * *